United States Patent [19]

Molloy

[11] 4,098,890

[45] Jul. 4, 1978

[54] METHOD FOR TREATING ARRHYTHMIA

[75] Inventor: Bryan B. Molloy, Indianapolis, Ind.

[73] Assignee: Eli Lilly and Company, Indianapolis, Ind.

[21] Appl. No.: 690,707

[22] Filed: May 27, 1976

Related U.S. Application Data

[62] Division of Ser. No. 536,283, Dec. 24, 1974, Pat. No. 3,987,201.

[51] Int. Cl.$^2$ ............... A61K 9/22; A61K 31/445; A61K 31/535; A61K 31/40
[52] U.S. Cl. ............... 424/248.4; 424/267; 424/274; 424/330
[58] Field of Search ............ 424/248, 267, 274, 248.4

[56] References Cited

U.S. PATENT DOCUMENTS

| | | | |
|---|---|---|---|
| 2,410,469 | 11/1946 | VanZoeren | 424/330 X |
| 3,395,146 | 7/1968 | Satzinger | 260/247.2 |
| 3,412,091 | 11/1968 | Moffett | 260/247.1 |
| 3,433,836 | 3/1969 | Petracek | 260/570 |
| 3,923,813 | 12/1975 | VanHoof et al. | 260/293.62 |
| 3,923,815 | 12/1975 | VanHoof et al. | 260/293.62 |
| 3,923,887 | 12/1975 | VanHoof et al. | 260/562 N |
| 3,972,935 | 8/1976 | Molloy | 260/570 R |
| 3,987,201 | 10/1976 | Molloy | 424/330 |

FOREIGN PATENT DOCUMENTS

| | | |
|---|---|---|
| 708,771 | 5/1954 | United Kingdom. |
| 923,942 | 4/1963 | United Kingdom. |
| 1,025,041 | 4/1966 | United Kingdom. |

OTHER PUBLICATIONS

J. Med. Chem. 271-6, Blank et al. (1969).

*Primary Examiner*—Leonard Schenkman
*Attorney, Agent, or Firm*—Charles W. Ashbrook; Walter E. Buting; Everet F. Smith

[57] ABSTRACT

Cardiac arrhythmia is treated orally or parenterally with diarylalkylamines and diarylalkenylamines.

8 Claims, No Drawings

METHOD FOR TREATING ARRHYTHMIA

This is a division of application Ser. No. 536,283, filed Dec. 24, 1974 now U.S. Pat. No. 3,987,201.

BACKGROUND OF THE INVENTION

This invention provides a method of treating cardiac arrhythmia. In particular, the invention provides a method of treatment of arrhythmia comprising administering to a subject suffering from an arrhythmia and in need of said treatment an effective amount of a diarylalkylamine or diarylalkenylamine, thereby converting the arrhythmia to a normal sinus rhythm of the heart.

While the direct causes of arrhythmia remain unknown, several treatments are currently available for converting an arrhythmia to a normal rhythm. The treatment of arrhythmia requires restoring the abnormal rhythm of the heart muscle to normal. No drug has yet been found which is totally effective for treating all types of arrhythmias. Several currently available drugs, such as quinidine, lidocaine, procainamide, and the like, are used to combat arrhythmia; however, the various undesirable side effects of these agents often limit their continued use. Several alkylenediamines have recently been prepared and evaluated as antiarrhythmic agents. Of particular importance among these are certain N,N-dialkyl-$N^1$-(2-indanyl)-$N^1$-aryl-1,3-propanediamines; see for example, Canadian Pat. No. 910,907.

It is an object of this invention to provide a new method for treating arrhythmia, which method comprises administering a compound selected from among a class of diarylalkylamines or diarylalkenylamines. Several such amines are available and have been widely tested pharmacologically and found to possess various activities. For example, numerous 3,3-diphenylpropylamines have been prepared and tested as analgesics. A complete review of this class of compounds has been compiled by Paul A. J. Janssen, Synthetic Analgesics Part 1, Diphenylpropylamines, Pergamon Press, 1960. Several 4,4-diphenylbutylamines and 5,5-diphenylpentylamines have been prepared and tested by Morikawa, Yakngaku Zasshi 80 475–480 (1960); cf Chemical Abstracts, 50, 5656e. Adamson also prepared several diarylpropylamines, diarylbutenylamines, and diarylbutylamines, as described in British Pat. No. 624,117. Additionally, diarylalkylamines and diarylalkenylamines havebeen prepared and studied by Marxer, Helv. Chem. Acta., 24, 209–225D (1941), and by Blank et al., J. Med. Chem., 271–276 (1969). Hodge prepared several halogenated diarylalkylamines and tested them as bactericides, as described in United States Pat. No. 2,681,934. Diarylalkylamines and diarylalkenylamines are reported to be generally useful as antihistamines, anticholinergic agents, local anesthetics, antispasmodic agents, and for treating asthma. According to Janssen, N,N-diisopropyl-3,3-diphenylpropylamine hydrochloride is the most active antispasmodic and antinicotinic agent of the diarylpropylamine series. Additionally, Janssen reported that N-(3,3-diphenylpropyl)piperidine hydrochloride displays weak antispasmodic, antihistaminic, parasympatholytic, antinicotinic, and local anaesthetic activities.

Diarylalkylamines and diarylalkenylamines have not heretofore been used as antiarrhythmic agents. The purported activities possessed by these classes of compounds in no way suggest that they would display a beneficial effect upon the cardiac muscle. An object of this invention is to provide a method of treating arrhythmia comprising adnimistering to a subject an effective amount of a diarylalkylamine or diarylalkenylamine.

SUMMARY OF THE INVENTION

This invention provides a method of treating arrhythmia which comprises administering to a subject suffering from an arrhythmia and in need of treatment an effective amount of a compound of the formula

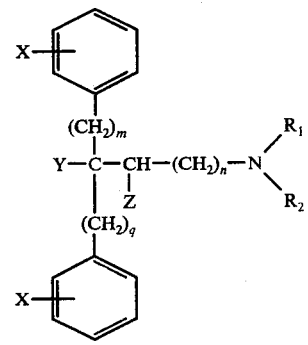

in which $n$ is 1, 2, or 3, $m$ is 0, 1, 2, or 3, $q$ is 0 or 2, and $m$ plus $n$ is greater than 1 and less than 6; X is hydrogen, fluorine, chlorine, bromine or iodine; Y and Z each are hydrogen or, taken together, form a double bond; and $R_1$ and $R_2$ independently are hydrogen, $C_1$–$C_6$ alkyl, or —$CH_2R_3$, in which $R_3$ is $C_2$–$C_5$ alkenyl, or $R_1$ and $R_2$ taken together with the adjacent nitrogen atom form a nitrogen containing heterocyclic ring selected from among piperidino, pyrrolidino, and morpholino. The pharmaceutically acceptable salts of the amines having the above formula are also useful as antiarrhythmic agents and are also embodied within the scope of this invention. According to this invention, a compound of the above formula, or a pharmaceutically acceptable salt thereof, is administered orally or parenterally to a subject suffering from an arrhythmia and in need of said treatment.

DETAILED DESCRIPTION OF THE INVENTION

In the above formula, $R_1$ and $R_2$ independently are hydrogen, $C_1$–$C_6$ alkyl, —$CH_2R_3$, in which $R_3$ is $C_2$–$C_5$ alkenyl, or $R_1$ and $R_2$ taken together with the adjacent nitrogen atom form a ring system selected from among pyrrolidino, piperidino, and morpholino. Examples of "$C_1$–$C_6$ alkyl" include groups such as methyl, ethyl, n-propyl, isopropyl, n-butyl, isobutyl, tert.-butyl, n-pentyl, isopentyl, 2-methylbutyl, n-hexyl, 2-methylpentyl, 3-methylpentyl, isohexyl, and like groups. Typical example of "$C_2$–$C_5$ alkenyl" include ethene, 1-propene, 2-propene, 2-butene, 3-pentene, and similarly, examples of "—$CH_2R_3$" include groups such as allyl, 2-butenyl, 3-butenyl, 3-pentenyl, 4-pentenyl, 2-hexenyl, 3-hexenyl, 2-methyl-2-butenyl, 2-ethyl-2-butenyl, 3-methyl-2-pentenyl, and the like.

The pharmaceutically acceptable salts of the amines having the above formula are useful as antiarrhythmic agents and are included within the scope of this invention. The term "pharmaceutically acceptable salt" as used herein, refers to salts of the amine bases of the above formula which are substantially non-toxic to living organisms. Typical pharmaceutically acceptable salts include those salts prepared by reaction of the diarylalkylamines and diarylalkenylamines of the above formula with acids, including mineral acids such as hydrochloric acid, hydrobromic acid, sulfuric acid, phosphoric acid, and the like; as well as those salts prepared by reaction of the amine with an organic acid such as acetic acid, oxalic acid, butyric acid, malonic acid, succinic acid, benzoic acid, naphthalenesulfonic acid, and the like. Also included within the term "pharmaceutically acceptable salts" are the quaternary ammonium salts. Examples of preferred quaternary ammonium salts include those prepared by reaction of an amine with a $C_1$–$C_4$ alkyl alkylating agent, such as methyl iodide, ethyl bromide, n-propyl chloride, isopropyl iodide, n-butyl bromide, methyl sulfate, isobutyl sulfonate, and the like. Other anions associated with the quaternary nitrogen atom can include hydroxide, nitrate, benzenesulfate, acetate, butyrate, and the like.

The diarylalkylamines and diarylalkenylamines having the above formula are prepared by any of a number of well known procedures. For example, a diarylalkyl halide, such as 4,4-diphenylbutylchloride for instance, can be reacted with an amine, such as diethylamine or the like, thereby displacing the halogen atom from the diarylbutylchloride and forming the corresponding diarylalkylamine. Similarly, diarylalkenyl halides can be reacted with an amine to form the corresponding diarylalkenylamines, which can then be reduced, for example by catalytic hydrogenation, to provide the corresponding diarylalkylamine.

A group of preferred compounds useful for treating arrhythmia according to this invention is represented by the above formula wherein $m$ and $q$ each are 0 and X is hydrogen or fluorine. Among this preferred group of antiarrhythmic agents, the compounds wherein $n$ of the above formula is 2 or 3 are particularly preferred.

An especially preferred group of compounds which are particularly suited to treating arrhythmia according to this invention are represented by the above formula wherein $m$ and $q$ each are 0, $n$ is 2, X is hydrogen, Y and Z each are hydrogen, and $R_1$ and $R_2$ are $C_1$–$C_6$ alkyl.

Typical examples of compounds having the above formula which are useful in treating arrhythmia according to this invention include:
N,N-diethyl-4,4-diphenylbutylamine;
N,N-dimethyl-5,5-diphenylpentylamine;
N,N-diisopropyl-4,4-diphenylbutylamine;
N,N-di-n-butyl-4,4-diphenylbutylamine;
N-methyl-4,4-diphenylbutylammonium chloride;
N-isopropyl-4,4-diphenylbutylamine;
N-(4,4-diphenylbutyl) piperidine;
N-(3-butenyl)-4,4-diphenyl-3-butenylamine;
N-allyl-4,4-diphenylbutylamine;
N-n-butyl-4,4-diphenylbutylamine;
N-butyl-N-methyl-4,4-diphenyl-3-butenylamine;
N,N-diethyl-4,5-diphenyl-3-pentenylamine;
N-isobutyl-N-hexyl-N-methyl-4,4-diphenylbutylammonium iodide;
N-tert.-butyl-N-methyl-4,4-diphenylbutylamine;
N,N-dimethyl-4,6-diphenyl-3-hexenylamine;
N-methyl-4,4-bis-(4-fluorophenyl)butylamine;
N,N-diisopentyl-4,4-bis-(4-chlorophenyl)butylamine;
N-ethyl-4,4-bis-(4-fluorophenyl)butylammonium bromide;
N,N-diisopropyl-5,5-diphenylpentylamine;
N-methyl-5,5-diphenyl-4-pentenylamine;
N,N-dipentyl-5,5-diphenylpentylamine;
N,N-diisohexyl-4,4-diphenylbutylammonium chloride;
N-n-propyl-4,4-diphenylbutylamine;
N,N,N-trimethyl-4,4-diphenylbutylammonium methanesulfate;
N,N-diethyl-4-phenethyl-6-phenylhexylamine;
N-(3-hexenyl)-N-butyl-3,4-diphenylbutylamine;
N,N-diisopropyl-4-phenethyl-6-phenylhexylamine;
N-(3,5-diphenyl-2-pentenyl)pyrrolidine;
N,N-diethyl-5,7-diphenylheptylamine;
N-(4,4-diphenylbutyl)morpholine;
N,N-diethyl-5,7-diphenyl-4-heptenylamine;
N-tert-butyl-4,4-diphenylbutylamine;
N,N-dimethyl-4,7-diphenyl-3-heptenylamine;
N,N-diisopropyl-4,6-diphenylhexylamine;
N,N-diisopropyl-4,5-diphenylpentylamine;
N-methyl-5,6-diphenylhexylamine;
N,N-diisopropyl-5,6-diphenylhexylamine;
N-methyl-3,5-bis-(4-chlorophenyl)pentylamine;
N-methyl-4-(4-fluorophenethyl)-6-(4-fluorophenyl)hexylamine;
N-n-hexyl-4-(3-bromophenethyl)-6-(3-bromophenyl)hexylamine;
N-pentyl-N-(4-hexenyl)-3,4-diphenylbutylamine;
N,N-diisopropyl-4,4-diphenyl-3-butenylamine;
N,N-dipentyl-4,5-bis-(4-bromophenyl)pentylamine;
N,N-diisobutyl-4,4-diphenylbutylamine;
4,5-bis-(4-iodophenyl)pentylamine;
N,N-dimethyl-5,5-diphenyl-4-pentenylamine;
5,6-diphenylhexylamine;
N,N-diallyl-4,4-diphenylbutylamine;
N-butyl-N-(3-hexenyl)-4,5-diphenyl-3-pentenylamine;
N,N-diisohexyl-3,4-diphenylbutylamine;
N,N-diallyl-4,4-diphenyl-3-butenylammonium acetate;
N,N-dimethyl-4,6-diphenylhexylamine;
N,N-di-3-hexenyl-4,4-diphenyl-3-butenylammonium nitrate;
N,N-diisopentyl-4,4-diphenylbutylamine;
N,N,N-tripropyl-5,5-diphenyl-4-pentenylammonium iodide; and
N-4,4-bis-(4-bromophenyl)-3-butenyl-N-methyl-piperidinium bromide In accordance with the present invention, an effective amount of a diarylalkylamine or diarylalkenylamine having the above formula, or a pharmaceutically acceptable salt thereof, is administered to a subject suffering from an arrhythmia and in need of said treatment. The compound can be administered in a variety of ways, including parenteral and oral administration. The compound is suitably formulated with any of a number of pharmaceutical diluents, carriers, or vehicles, thereby facilitating convenient administration to a subject. A subject suffering from an arrhythmia and in need of treatment is typically treated according to this invention by administering intravenously a suitably formulated compound of the above formula until correction of the arrhythmia is effected, and maintenance therapy can then be achieved by orally administering a compound of the above formula suitably formulated for oral administration.

According to this invention, therapeutic and prophylactic arrhythmia treatment can be achieved by orally administering an amine having the above formula.

Prophylactic arrhythmia treatment can be accomplished, for example by one skilled in treating subjects suspected of developing an arrhythmia, by administering to a subject a compound having the above formula, ideally formulated for convenient oral administration. It will be understood that the particular dosage regimen required to treat a subject in need of treatment, either therapeutically or prophylactically, will depend upon the particular conditions surrounding a specific case, such as the subject being treated, the route and frequency of administration, the extent of treatment required, and the like. These considerations will be determined by the person skilled in the art who is recommending the treatment in each specific case.

The present invention accordingly provides a pharmaceutical composition which comprises a diarylalkylamine or diarylalkenylamine having the above formula, or a salt thereof, in association with a suitable pharmaceutical vehicle, carrier, or diluent. Typical vehicles, carriers, or diluents commonly incorporated with the above-described amines in a pharmaceutical composition according to this invention include lactose, dextrose, sucrose, sorbital, mannitol, propylene glycol, calcium silicate, potato starch, sodium chloride, and the like.

In carrying out the new method for treating arrhythmia according to this invention, a diarylalkylamine or diarylalkenylamine having the above formula is formulated for convenient administration to a subject suffering from an arrhythmia, and the pharmaceutical composition is administered to the subject such that the amount of active ingredient administered per day is within the range of about 100 mg. to about 1000 mg. The normal dose will generally amount to about 200 to 300 mg., administered from 2 to 3 times per day for the therapeutic conversion of an arrhythmia to a normal rhythm, and generally from 1 to 2 times per day for the prophylactic control of arrhythmia.

For the oral administration of the antiarrhythmic agent according to this invention, the compound of the above formula is formulated with a suitable carrier or diluent and molded into a tablet, or encapsulated into an empty telescoping gelatin capsule, or mixed with suitable diluents to form a solution or suspension. A typical formulation for oral administration, for example, comprises a compound of the above formula in the amount of about 200 mg.; about 150 mg. of dextrose; and 500 mg. of starch powder.

Parenteral administration according to this invention is accomplished with a lyophilized diarylalkylamine or diarylalkenylamine of the above formula, for example in the amount of about 100 mg., mixed with a diluting solution containing a diluent such as sodium chloride, in the amount of about 10 mg., in about 100 ml. of sterile water. Ampoules of the antiarrhythmic agent contain about 100 mg. of active ingredient admixed with a diluent such as mannitol, in the amount of about 80 mg., and a diluting solution as above. Alternatively, sterile water can be added to the ampoule contents just prior to use. The aqueous solution can be intravenously administered to a subject suffering from arrhythmia over a period of about 2 to 6 hours.

The method of treating arrhythmia according to this invention was demonstrated by a series of experiments in dogs. An experimentally induced arrhythmia in a dog was converted to normal rhythm as demonstrated in the following experiment.

Mongrel dogs of either sex were anesthetized with pentobarbital-sodium at a dose of about 35 mg. per Kg. of body weight. The dogs were maintained on positive pressure respiration during the experiment. An arrhythmia was induced in each dog by intravenously injecting a sufficient amount of ouabain to induce an arrhythmia. The cardiac activity was monitored by electrocardiogram. Severe ventricular arrhythmia generally appeared in each dog after about ten minutes following the injection of the ouabain. Doses of a diarylalkylamine or diarylalkenylamine having the above formula sufficient to convert the arrhythmia to normal rhythm were administered as an intravenous infusion. Conversion of the arrhythmia to normal rhythm was observed by electrocardiogram monitoring, and following conversion of the arrhythmia to normal rhythm, an additional identical dose of the antiarrhythmic agent was administered.

Table I shows the tests results of several experiments carried out as described hereinabove. The term "Converting Dose" refers to the initial dose of antiarrhythmic agent needed to convert the arrhythmia to a normal rhythm. "Total Dose" is the sum of the initial converting dose and the subsequent identical dose of antiarrhythmic agent. "Duration of Conversion" refers to the time in minutes that a normal sinus rhythm was maintained following the conversion of the arrhythmia. In several experiments, the duration of conversion was longer than 120 minutes, after which time the experiment was terminated.

Table I

| Antiarrhythmic Agent | Ouabain Dose mg/Kg. | Converting Dose mg/Kg. | Total Dose mg/Kg. | Duration of Conversion Minutes |
| --- | --- | --- | --- | --- |
| N,N-diisopropyl-4,4-diphenylbutylamine | 60 | 1.5 | 3.0 | >120 |
| N-butyl-4,4-diphenylbutylamine | 60 | 0.6 | 1.2 | >120 |
| N-tert.-butyl-4,4-diphenylbutylamine | 60 | 2.3 | 4.6 | >120 |
| N,N-diisopropyl-5,5-diphenylpentylamine | 55 | 4.5 | 9.0 | 109 |
| N,N-diisopropyl-4,4-diphenyl-3-butenylamine | 50 | 2.75 | 5.5 | 40 |
| N,N-diisopropyl-4,6-diphenylhexylamine | 55 | 1.8 | 3.6 | >120 |
| N-methyl-4,4-bis-(4-fluorophenyl)-butylamine | 50 | 2.0 | 4.0 | >120 |
| N-methyl-4,7-diphenylheptylamine | 50 | 4.75 | 9.5 | >120 |

I claim:
1. A method for treating arrhythmia comprising administering to a subject suffering from an arrhythmia and in need of treatment an effective amount of a compound of the formula

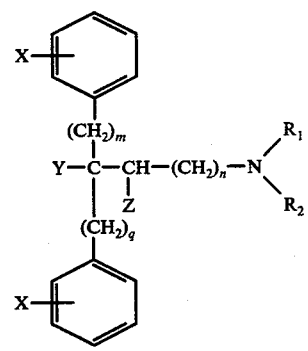

wherein: $n$ is 1, 2, or 3; $m$ is 0, 1, 2, or 3; $q$ is 0 or 2; and $m$ plus $n$ is greater than 1 and less than 6;

X is hydrogen, fluorine, chlorine, bromine, or iodine;

Y and Z each are hydrogen or, taken together, form a double bond;

$R_1$ and $R_2$ taken together with the adjacent nitrogen atom form a heterocyclic ring system selected from the group consisting of piperidino, pyrrolidino, and morpholino; and the pharmaceutically acceptable salts thereof.

2. The method according to claim 1 wherein in the formula representing the compound administered, $q$ is 0 and X is hydrogen or fluorine.

3. The method according to claim 2 wherein in the formula representing the compound administered, $m$ is 0.

4. The method according to claim 3 wherein in the formula representing the compound administered, $n$ is 2.

5. The method according to claim 4 wherein in the formula representing the compound administered, X is hydrogen.

6. The method according to claim 5 wherein in the formula representing the compound being administered, Y and Z each are hydrogen.

7. The method according to claim 1 wherein the compound is administered orally.

8. The method according to claim 1 wherein the compound is administered parenterally.

* * * * *